United States Patent [19]
Haber et al.

[11] Patent Number: 5,458,576
[45] Date of Patent: Oct. 17, 1995

[54] SAFETY SYRINGE WITH RETRACTING NEEDLE

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 171,356

[22] Filed: Dec. 22, 1993

[51] Int. Cl.⁶ ..................................... A61M 5/00
[52] U.S. Cl. .................. 604/110; 604/218; 604/222; 604/195
[58] Field of Search ................... 604/110, 187, 604/263, 218, 220, 221, 222, 195, 198

[56] References Cited

U.S. PATENT DOCUMENTS

| | | |
|---|---|---|
| 4,507,117 | 3/1985 | Vining . |
| 4,826,489 | 5/1989 | Haber et al. . |
| 4,966,593 | 10/1990 | Lennox . |
| 5,013,301 | 5/1991 | Marotta, Jr. . |
| 5,064,419 | 11/1991 | Gaarde . |
| 5,084,018 | 1/1992 | Tsao ........................................ 604/110 |
| 5,085,640 | 2/1992 | Gibbs . |
| 5,114,410 | 5/1992 | Batlle ..................................... 604/195 |
| 5,122,118 | 6/1992 | Haber et al. . |
| 5,180,369 | 1/1993 | Dysarz .................................... 604/110 |
| 5,190,526 | 3/1993 | Murray et al. ......................... 604/110 |

OTHER PUBLICATIONS

Engineering sketch of Braun two-piece syringe dated 16 Dec. 1993.

Primary Examiner—John D. Yasko
Attorney, Agent, or Firm—Townsend and Townsend and Crew

[57] ABSTRACT

A retracting needle safety syringe (2) includes a barrel (4) having a tip (10), to which a needle assembly (28) is mounted, and a plunger (6) including a stem (34) and a piston (40) at the distal end of the stem. The piston has a piston body (46) and a piston seal (58) which engages the barrel inner surface. The piston seal is detached from the piston, the piston body is secured to the tip, and the tip of the barrel is detached from the remainder of the barrel when the plunger is moved to its distal position. Pulling the plunger proximally from the distal position back towards a proximal position causes the piston body, the tip and needle assembly to be pulled into the interior (56) of the barrel, but without the piston seal sliding against the barrel. This retraction can take place manually or automatically.

32 Claims, 10 Drawing Sheets fig. 1 fig. 2 fig. 3 fig. 4 fig. 5 fig. 6A  fig. 6B fig. 7 fig. 8 fig. 9 fig. 8A fig. 9A

SAFETY SYRINGE WITH RETRACTING NEEDLE

BACKGROUND OF THE INVENTION

The need to prevent health care workers from being injured by used needles is well recognized. One type of safety syringe allows the needle to be retracted into the barrel for disposal. See, for example, U.S. Pat. No. 4,507,117 to Vining, et al., U.S. Pat. No. 4,826,489 to Haber, et al. and U.S. Pat. No. 5,122,118 to Haber, et al.

One of the problems with conventionally designed safety syringes in which the needle is withdrawn into the barrel for safe disposal, is cost. That is, conventional designs, although perhaps effective, may be too costly to find widespread use as disposable syringes. Also, many safety syringes require the user to use the syringe differently than conventional syringes. This can also provide a disincentive to use the safety syringe.

SUMMARY OF THE INVENTION

The present invention is directed to a safety syringe in which the needle is retractable into the body for safe disposal. The syringe preferably looks and operates like a conventional syringe. In one embodiment, after an injection, the user merely pulls the plunger proximally to pull the needle assembly back into the barrel. No special twisting, turning or unlatching steps need to be done to disconnect the tip from the remainder of the barrel and allow the needle assembly to be withdrawn into the barrel. With a second embodiment, the needle assembly is automatically withdrawn back into the barrel once the plunger is in its second or distal position without any further action on the part of the user. The manually retracting version can be made using only two parts while the automatically retracting version can be made using only four parts to help achieve the desired low cost necessary for widespread use.

The safety syringe includes a barrel having a tip, to which a needle assembly is typically mounted, and a plunger including a stem and a piston at the distal end of the stem. The piston has a piston body and a piston seal which provides sealing engagement with the inner surface of the barrel. The tip of the barrel is detached from the remainder of the barrel when the plunger is in its fully forward or distal position. When at the distal position the plunger is secured to the tip so that withdrawing the plunger proximally from the distal position back towards a proximal position causes the tip and needle assembly therewith to be pulled into the interior of the barrel. The piston seal is manipulated prior to this proximal movement of the tip and needle assembly, so that the piston seal slides against the inner surface of the barrel during such proximal movement; this eliminates this frictional component to aid retraction of the needle into the barrel.

One of the primary features of the invention is the recognition that elimination of the sliding seal between the inner surface of the barrel and the piston seal when pulling the needle assembly into the barrel would be very desirable for the manually operated version and important for the automatically retracted version. In the preferred embodiment this is accomplished by completely separating the seal ring from the piston body by breaking a frangible connection between the two. Separating the piston seal from the piston body also helps to minimize the residual amount of the pharmaceutical in the syringe at the end of the injection stroke. It could also be accomplished by, for example, moving an O-ring type of piston seal from a first position along the piston body to a second position along the piston body; the second position would have a smaller diameter to permit the O-ring seal to contract when at the second position and thus disengage from the inner surface of the barrel.

The retraction of the barrel tip and needle assembly can take place manually by the user pulling on the plunger after the injection or automatically at the end of an injection stroke. To do so automatically, the piston is released from the distal end of the stem, which is hollow in this embodiment, when the plunger is in the distal position and the released piston, the barrel tip and needle assembly therewith are drawn back into the stem, typically by a spring.

The tip of the barrel is preferably coupled to the remainder of the barrel by a frangible connection that leaves an inner circular edge at the distal end of the barrel after the tip has been disconnected. The piston preferably includes an inwardly tapering annular surface which engages and dilates the inner circular edge so that the tip can be pulled into the barrel without interference at the site of the former frangible connection.

Another feature of the invention relates to the sequence of severing the frangible connections. Preferably the frangible connection between the piston seal and the piston body is severed prior to severing the frangible connection between the tip and the side wall of the barrel. This eliminates any pressure buildup between the distal face of the piston and the tip of the barrel as the plunger moves to the distal position. Any remaining fluid, which has been trapped between the two, can escape through the gap between the piston seal and the piston body created by the rupture of the piston frangible connection. This eliminates the pressurized expulsion of liquid from the syringe when the barrel frangible connection, between the tip and the side wall of the barrel, is broken. Another advantage of the sequential breaking of the frangible connections is that it reduces the peak force which must be applied to the plunger at the end of the stroke.

The syringe can be designed so that when the piston body engages the tip, the tip is canted or angled to one side once the barrel frangible connection between the tip and the side wall of the barrel is broken. This aids withdrawing the tip back through the inner circumferential edge created at the ruptured barrel frangible connection. The canting of the needle assembly can also cause the tip of the needle to engage the side wall of the barrel to prevent the needle assembly from being driven back through the open distal end of the barrel.

The connection between the plug portion of the piston body and the tip of the barrel is preferably a simple friction fit. While various types of detents, twist-latch engagement elements, etc. could be used, it is believed that the smooth operating motion achieved through the friction fit is especially desirable when aspirating liquid pharmaceuticals into the barrel of the needle assembly.

The stem may have a necked-down region adjacent the piston to permit the stem to be broken away from the piston once the piston body, barrel tip and needle assembly are housed within the barrel. This further helps prevent attempted reuse or misuse of the used syringe.

Other features and advantage of the invention will appear from the following description in which the preferred embodiment has been set forth in detail in conjunction with the accompanying drawings.

DESCRIPTION OF THE PREFERRED EMBODIMENT

Figure 1:
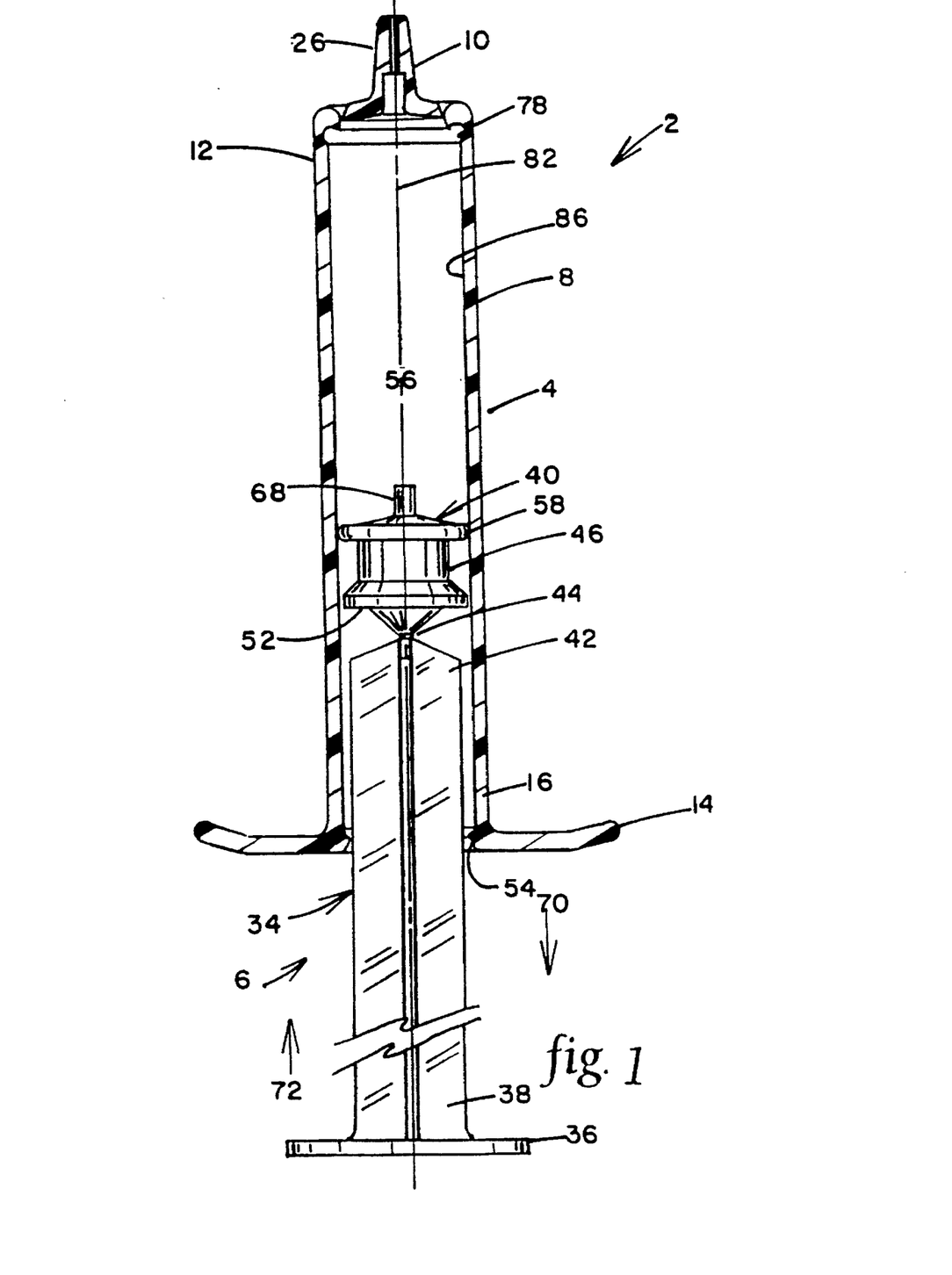
FIG. 1 is a side view of a safety syringe made according to the invention with the barrel shown in cross-section.

FIG. 1 illustrates a manually retractable safety syringe 2 including a barrel 4 and a plunger 6. Barrel 4 includes a generally cylindrical side wall 8 terminating at a tip 10 at the distal end 12 of side wall 8 and finger ledges 14 at the proximal end 16 of side wall 8.

Figure 2:
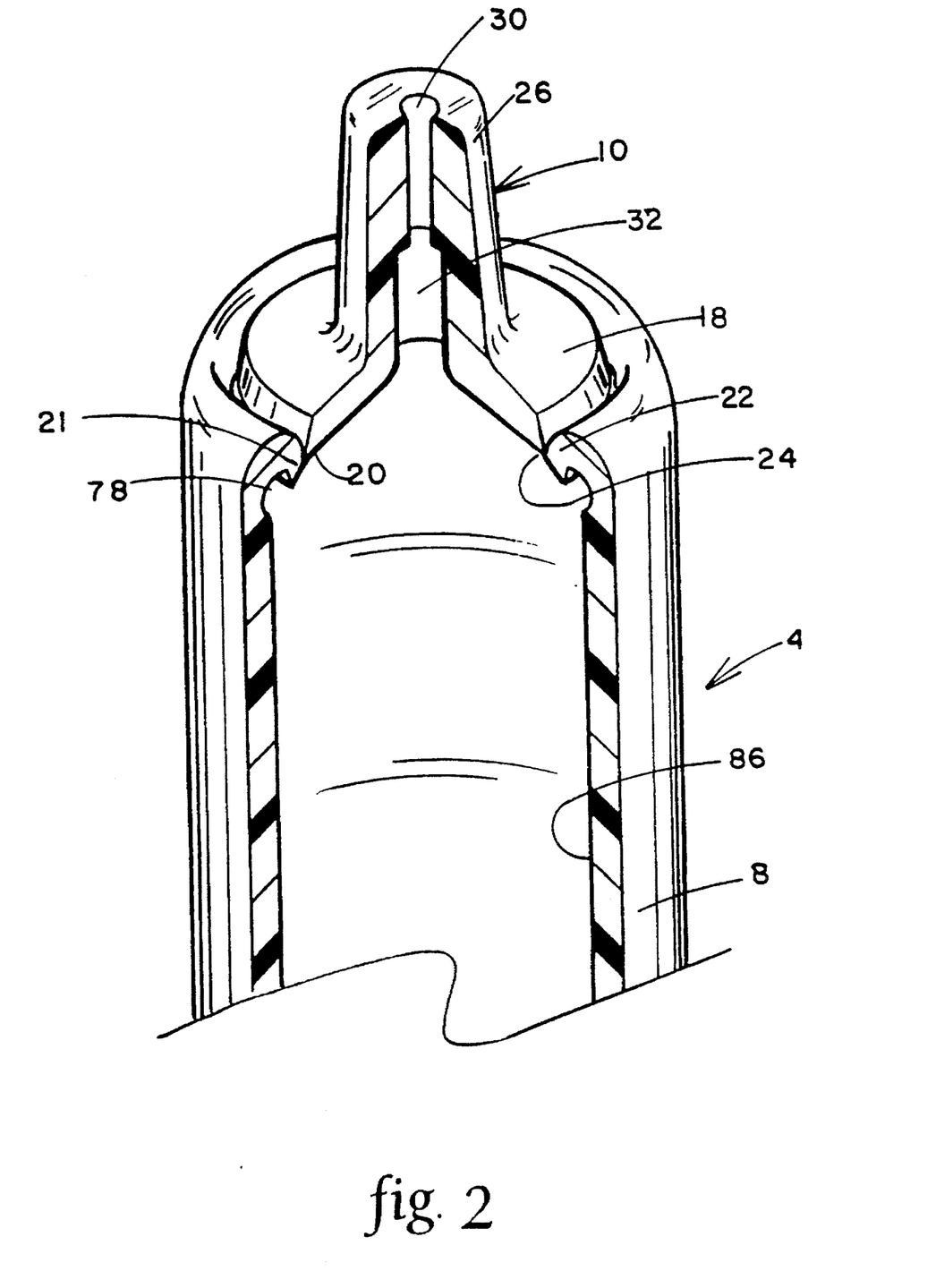
FIG. 2 is an enlarged isometric view of the distal end of the barrel of FIG. 1 with a quarter section removed.
Figure 5:
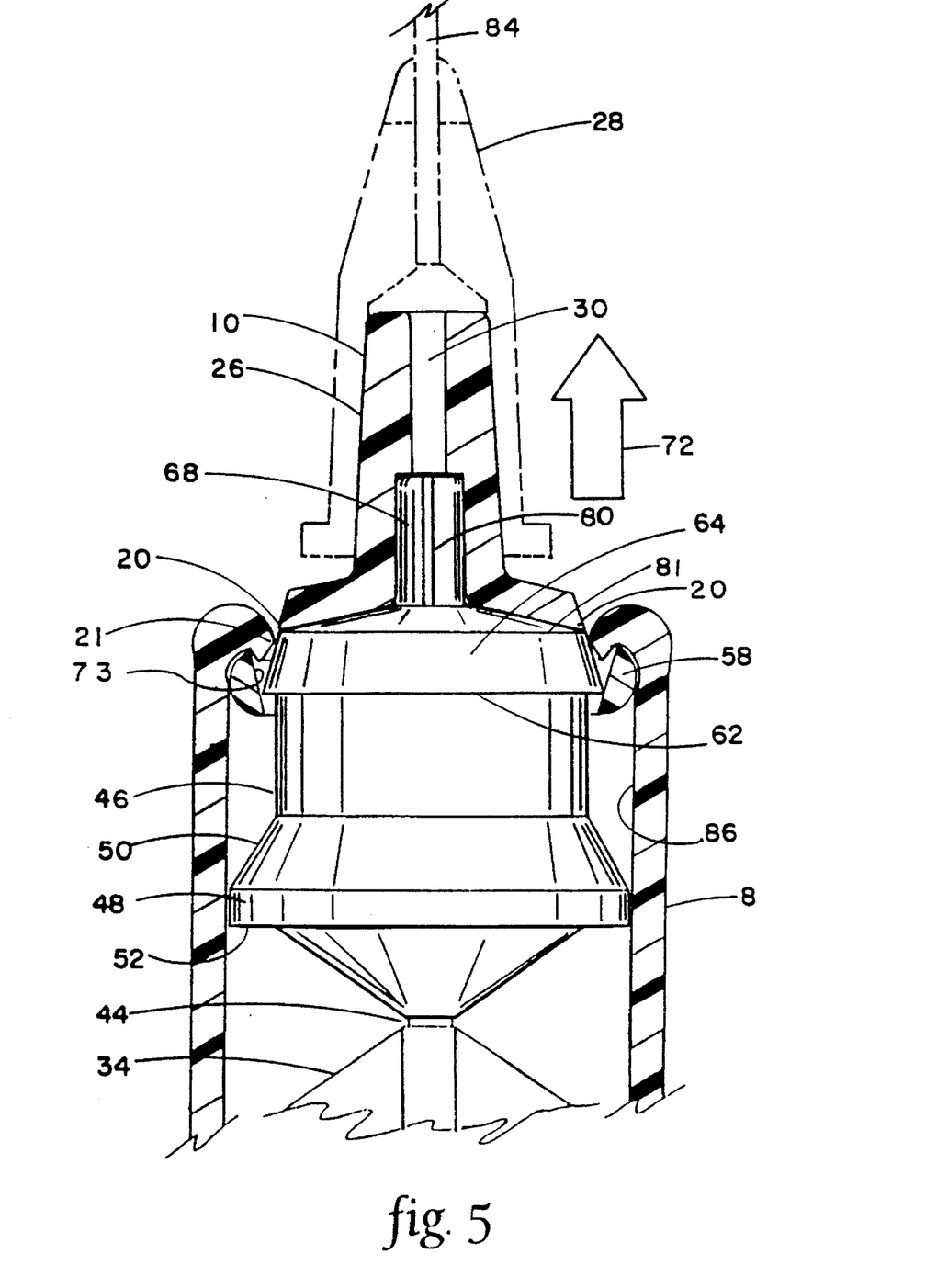
FIG. 5 is a view similar to that of FIG. 4 with the plunger in the second or distal position showing the rupture of the frangible connections between the piston seal and the piston body and between the barrel tip and the barrel side wall, the proximal portion of the needle assembly shown in phantom.

Barrel 4, as shown best in FIG. 2, includes a disk-like portion 18 having an outer circular edge 20 which is connected to an inner circumferential edge 21 of a rolled over lip portion 22 of side wall 8 at a barrel frangible connection 24. Frangible connection 24 has a nominal diameter about half way between the nominal diameters of edges 20, 21. Barrel tip 10 also includes a slightly tapered extension 26 over which a needle assembly 28, shown in phantom lines in FIG. 5, is mountable and is secured thereto through a friction fit. Extension 26 has a central bore 30, a portion of which is enlarged to create a plug receptacle 32, the use of which is described below.

Plunger 6 includes a generally cruciform stem 34 having a thumb pad 36 at the proximal end 38 of stem 34. Plunger 6 also includes a piston 40 secured to the distal end 42 of stem 34 at a necked down region 44. Necked down region 44 allows stem 34 to be broken away from piston 40 after use and prior to disposal.

Figure 3:
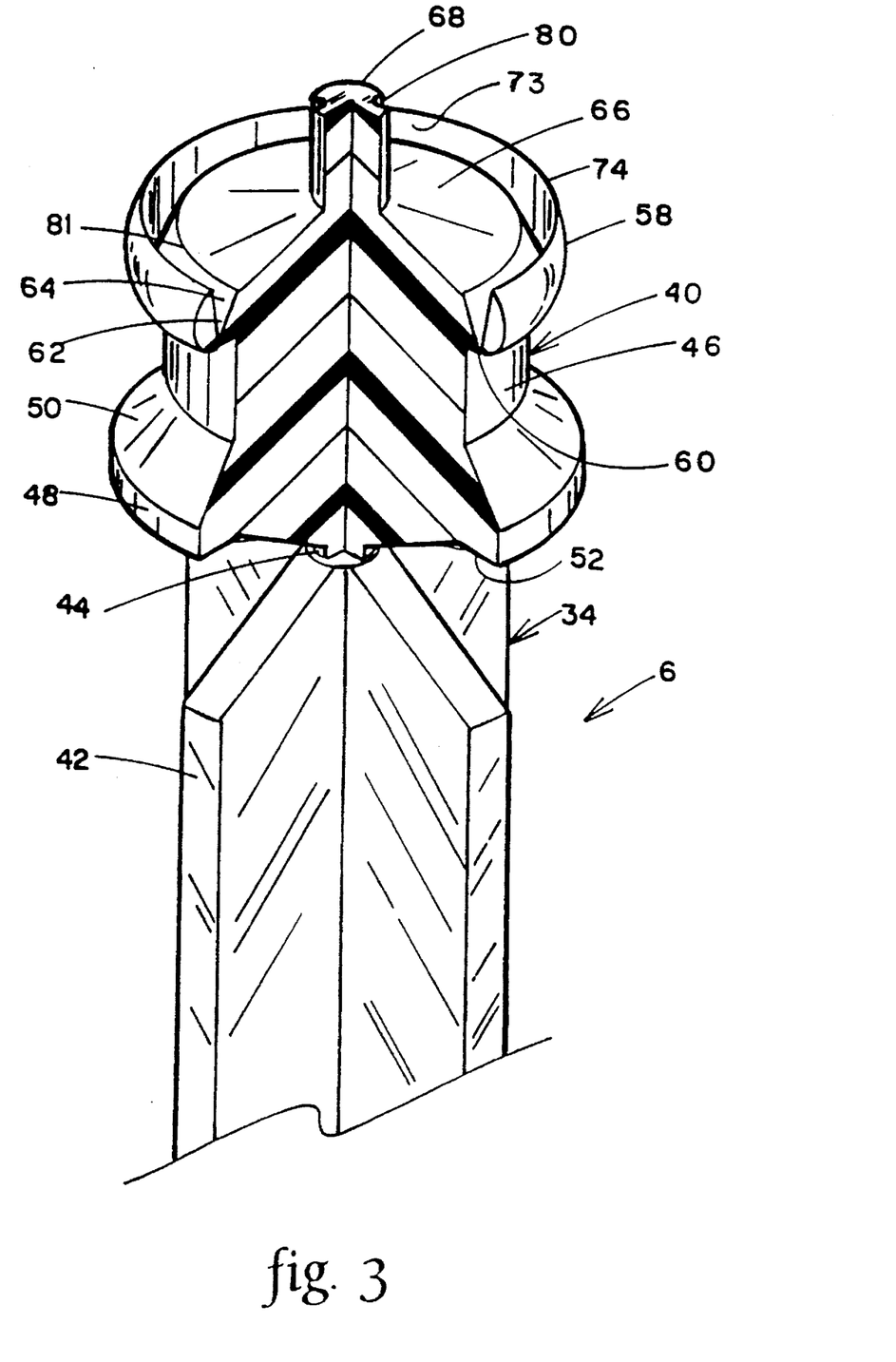
FIG. 3 is an enlarged isometric of the distal end of the plunger of FIG. 1 with a quarter section of the piston removed.

Piston 40 includes a piston body 46 having an alignment skirt 48 at its proximal end. Alignment skirt 48 has a tapered, distally facing surface 50 and a radially extending, proximally facing face 52. Tapering surface 50 permits alignment skirt 48 to move in distal direction 72 past the radially inwardly extending stop 54 at proximal end 16 of side wall 8 when inserting piston 40 into barrel 4 through open proximal end 16 of side wall 8. However, the radial nature of face 52 causes face 52 to solidly engage stop 54 upon movement of piston 40 in proximal direction 70 towards stop 54; this prevents removal of piston 40 from the interior 56 of barrel 4 through the opening at proximal end 16 of side wall 8.

Piston 40 also includes a piston seal 58 extending outwardly from annular piston frangible connection 60 at the proximal end 62 of an inwardly tapering annular surface 64, which is positioned adjacent the distal face 66 of piston 40. Piston 40 also includes a generally cylindrical plug 68 sized for a slight interference friction fit within receptacle 32.

Figure 4:
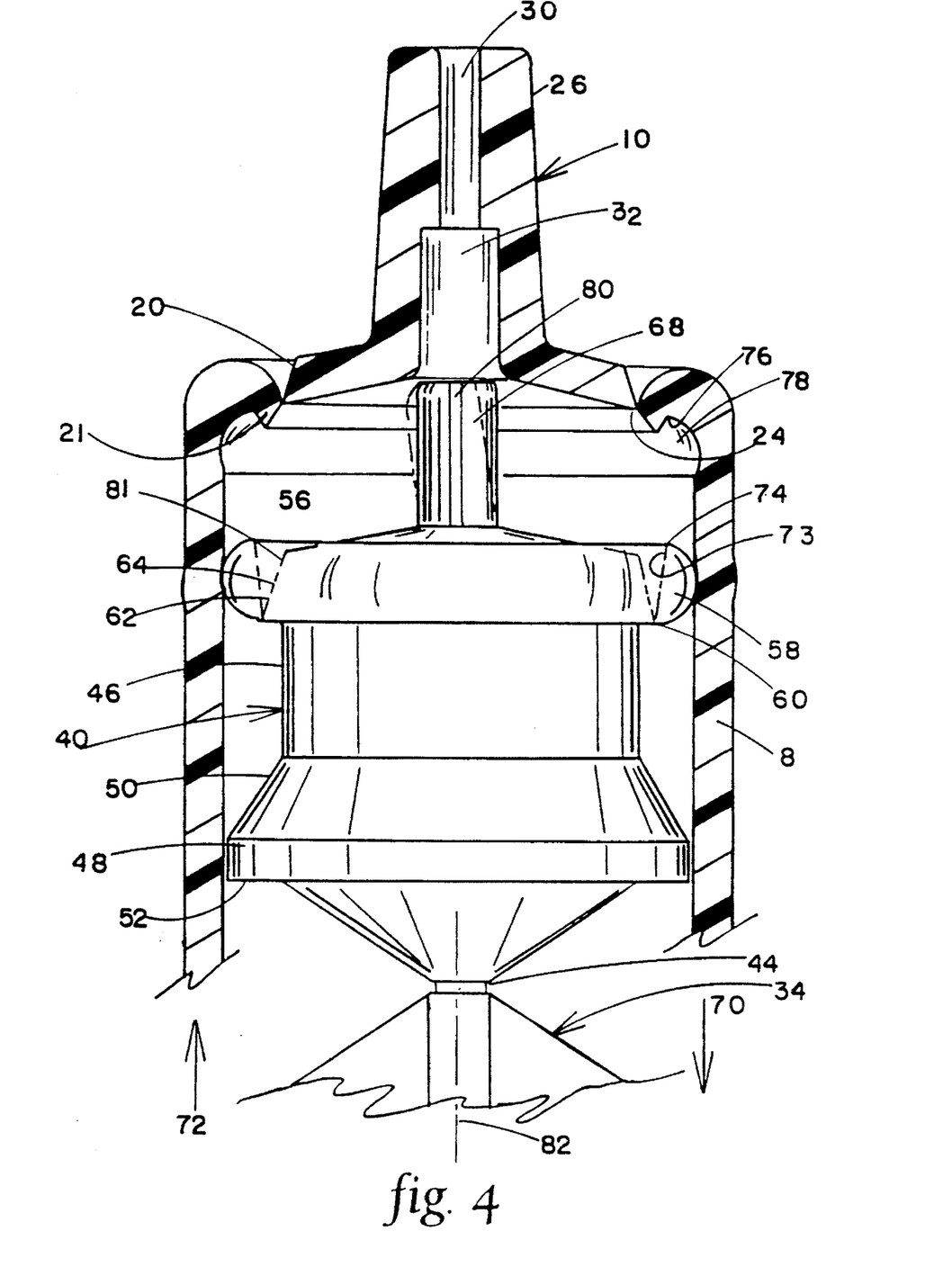
FIG. 4 is an enlarged view of the distal end of the syringe of FIG. 1 with the piston close to but not touching the tip of the barrel.

FIG. 4 illustrates the position of piston 40 with safety syringe 2 in an as-shipped condition. Preferably, barrel 4 and plunger 6 are both made of lubricous materials such as polypropylene or polyethylene. Piston seal 58 presses against side wall 8 with sufficient force to provide a good seal. If desired, plug 68 could be partially or fully inserted into receptacle 32 for shipment.

A needle assembly 28 is mounted to extension 26 of tip 10 as suggested in FIG. 5 and plunger 6 is moved in proximal direction 70 to aspirate an appropriate liquid pharmaceutical into interior 56 of barrel 4 in a conventional manner. An injection is then given, again in a conventional manner. During the injection stroke, the pressurized liquid within interior 56 between tip 10 and piston 40 presses against the inner surface 73 of piston seal 58 to bias seal 58 against inner surface 86 of sidewall 8.

At the end of the injection stroke, that is with plunger 6 moving in the distal direction 72, three things occur as the plunger moves to the second, or distal, position shown in FIG. 5. The first is the rupture or severing of piston frangible connection 60 upon the engagement of the distal edge 74 of piston seal 58 with the distal end 76 of an annular pocket 78 formed in inner surface 86 of side wall 8 adjacent lip potion 22. See FIG. 5. The rupture of piston frangible connection 60 provides an escape path for any pressurized fluid captured between tip 10 of barrel 4 and piston 40. Plug 68 has axially extending surface grooves 80 to keep from trapping fluid within central bore 30. Next, piston body 44 drives tip 10 distally, thus severing barrel frangible connection 24. Plunger 6 is then pushed a short distance further until tapering annular surface 64 engages inner circumferential edge 21 as shown in FIG. 5.

Distal edge 81 bounding annular surface 64 is somewhat smaller in diameter than is edge 21 while proximal end 62 of surface 64 has a larger diameter than edge 21. This causes surface 64 to expand or dilate edge 21 and smooth over the rough edges left by frangible connection 24 along edge 21. Piston body 46, tip 10 and needle assembly 28 therewith are pulled through the opening defined by edge 21 and into interior 56 of barrel 4 before the dilated material has had a chance to relax and possibly interfere with the movement into the interior of the barrel.

The use of a radially enlarged annular pocket 78 helps to retain piston seal 58 at distal end 12 of side wall 8 to minimize the frictional resistance to the movement of piston body 46, tip 10 and needle assembly 28 into interior 56. Retaining piston seal 58 within pocket 78 also keeps piston seal 58 from rattling around within barrel 4.

FIG. 4 illustrates in dashed lines plug 68 having a cant, that is being angled relative to axis 82 of syringe 2. Using a plug 68 having such a cant will cause tip 10 and needle assembly 28 therewith to cant or angle away from axis 82 when the position of FIG. 5. This will cause inner and outer circular edges 20, 21 to be offset to one another so to reduce the chance for frictional interference when moving tip 10 into interior 56. Also, depending on the amount of cant of plug 68 and the length of needle assembly 28, the tip of the needle 84 could be oriented adjacent the inner surface 86 of side wall 8 so that movement of stem 34 in distal direction 72 will cause the tip of needle 84 to be captured within annular pocket 78, thus preventing the reuse of syringe 2. Also to help prevent reuse of the syringe, the user can separate the stem 34 from piston body 46 at necked down region 44 after use.

Figures 6A, 6B:
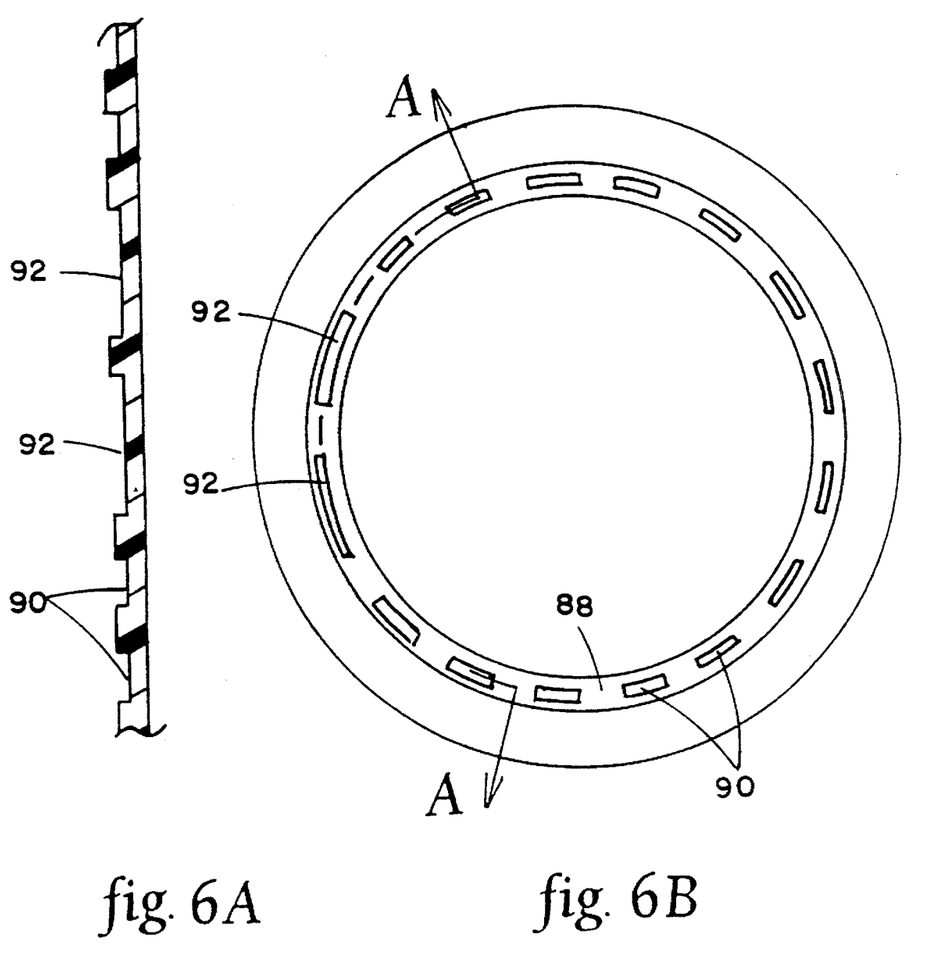
FIG. 6A is a cross-sectional view taken along line A—A of FIG. 6B.
FIG. 6B is a plan view of a generic frangible connection with a lower strength region to provide a site for initiation of failure of the frangible connection.
Figure 7:
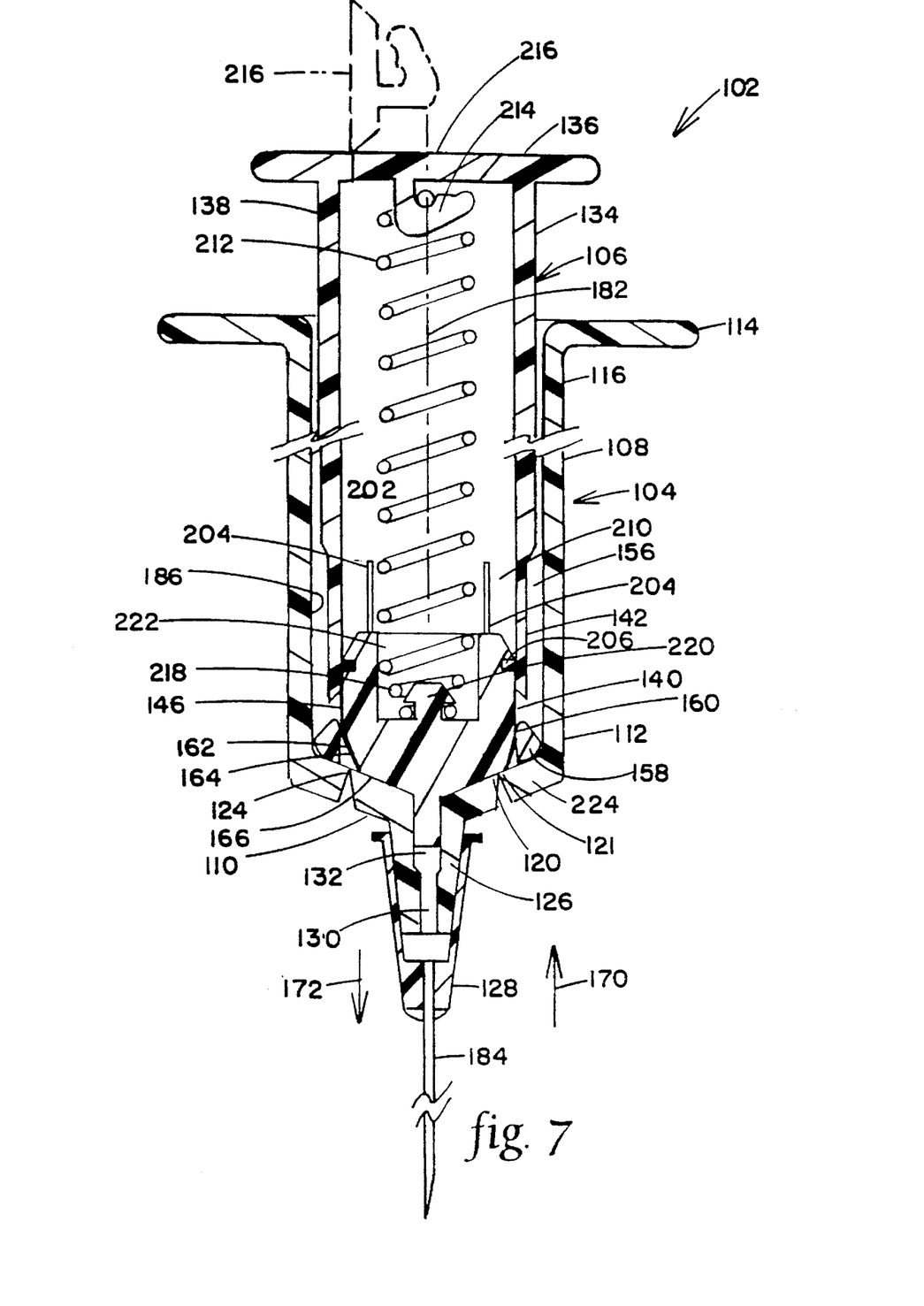
FIG. 7 is a side cross-sectional view of an alternative embodiment of the safety syringe of FIG. 1 in which the needle assembly is automatically retracted into the barrel upon placing the plunger in the distal or second position at the end of an injection, the syringe shown in the as-shipped condition.

Barrel frangible connection 24 and piston frangible connection 60 are, in the disclosed embodiment, of equal thicknesses along their respective lengths. However, it may be useful to vary the thickness, and thus the strength, of the frangible connections to provide a weaker region for the reliable initiation of the rupture of the frangible connection at a particular position along the frangible connection. In FIGS. 6A and 6B, a generic frangible connection 88 is seen to include a series of equal-size reduced thickness regions 90 along most of frangible connection 88. However, there is a pair of reduced thickness regions 92, each which has a much greater circumferential length than any of the other reduced thickness regions 90. This arrangement provides a site for the initiation of a failure of frangible connection 88 at regions 92.

FIGS. 7–9A disclose an alternative embodiment of safety syringe 2 in which a needle assembly is automatically withdrawn into the syringe when the plunger is in the distal position. Similar parts are referred to with corresponding 100 series reference numerals and will thus not be described in detail. As is evident from the figures, the primary difference is in the construction of plunger 106. Plunger 106 includes a hollow, cylindrical stem 134, having a hollow interior 202. The distal end 142 of stem 134 has an inner wall and the remainder of the stem has a number of axially extending slots 204 which permit distal end 142 to dilate. Piston 140 is removably mounted to distal end 142 of stem 134 through the engagement of radially inwardly directed projections 206 at the distal end 142 of stem 134 into hollow receptacles 208 formed in piston 140 as shown best in FIGS. 9A and 8A. The natural resilience of arms 210 formed by distal end 142 between slots 204 keeps piston 140 secured to the distal end during normal use.

Plunger 106 also includes a tension spring 212 secured at one end to a hook 214 extending from the distal surface of a central portion 216 of thumb pad 136. Central portion 216 is formed as a one-piece component with the remainder of thumb pad 136 and side wall 134 and is pivoted from the dashed line position of FIG. 7 to the solid line position of FIG. 7 during assembly. Central portion 216 is secured in place, such as through the use of an adhesive, ultrasonic welding or other suitable techniques. The distal end 218 of spring 212 is secured to a post 220 formed in a hollow receptacle 222 in piston 140. Once assembled in the pre-use or as-shipped position of FIG. 7, spring 212 biases piston 140 in proximal direction 170. Proximal movement of piston 140 within stem 134 is prevented through the engagement of projections 206 within receptacles 208.

Figure 8:
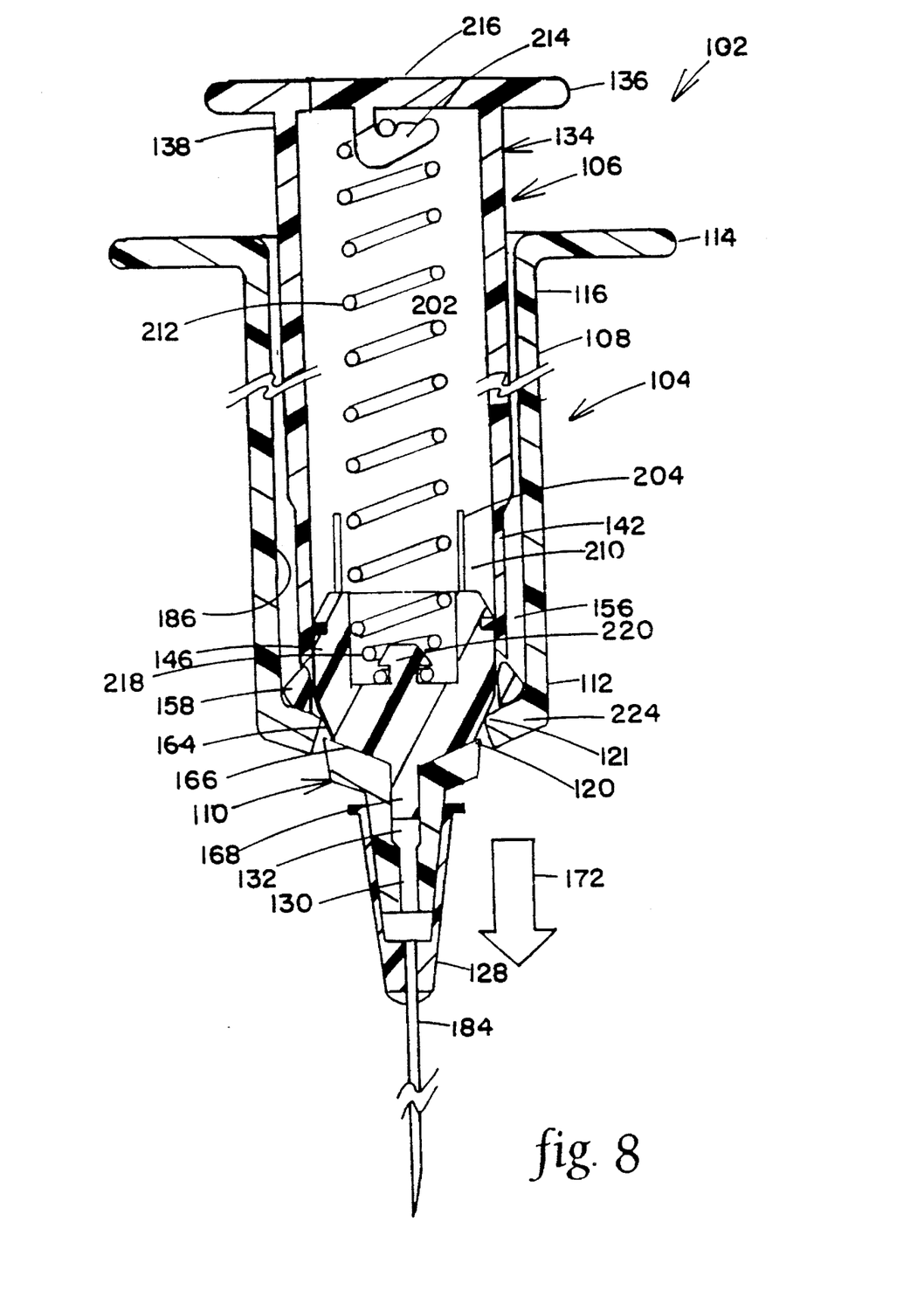
FIG. 8 illustrates the syringe of FIG. 7 at the termination of an injection and after the piston and barrel frangible connections have been broken.
Figure 8A:
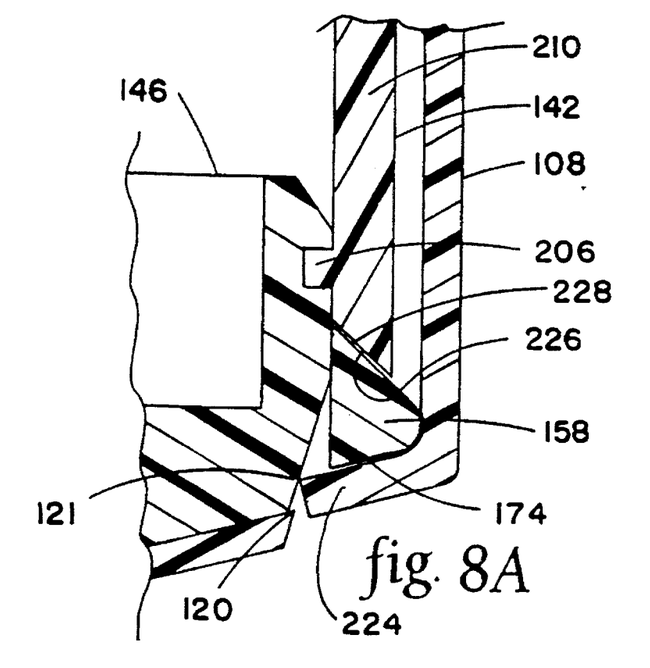
FIG. 8A is an enlarged view of a portion of the syringe of FIG. 8 illustrating the severed frangible connections.
Figure 9:
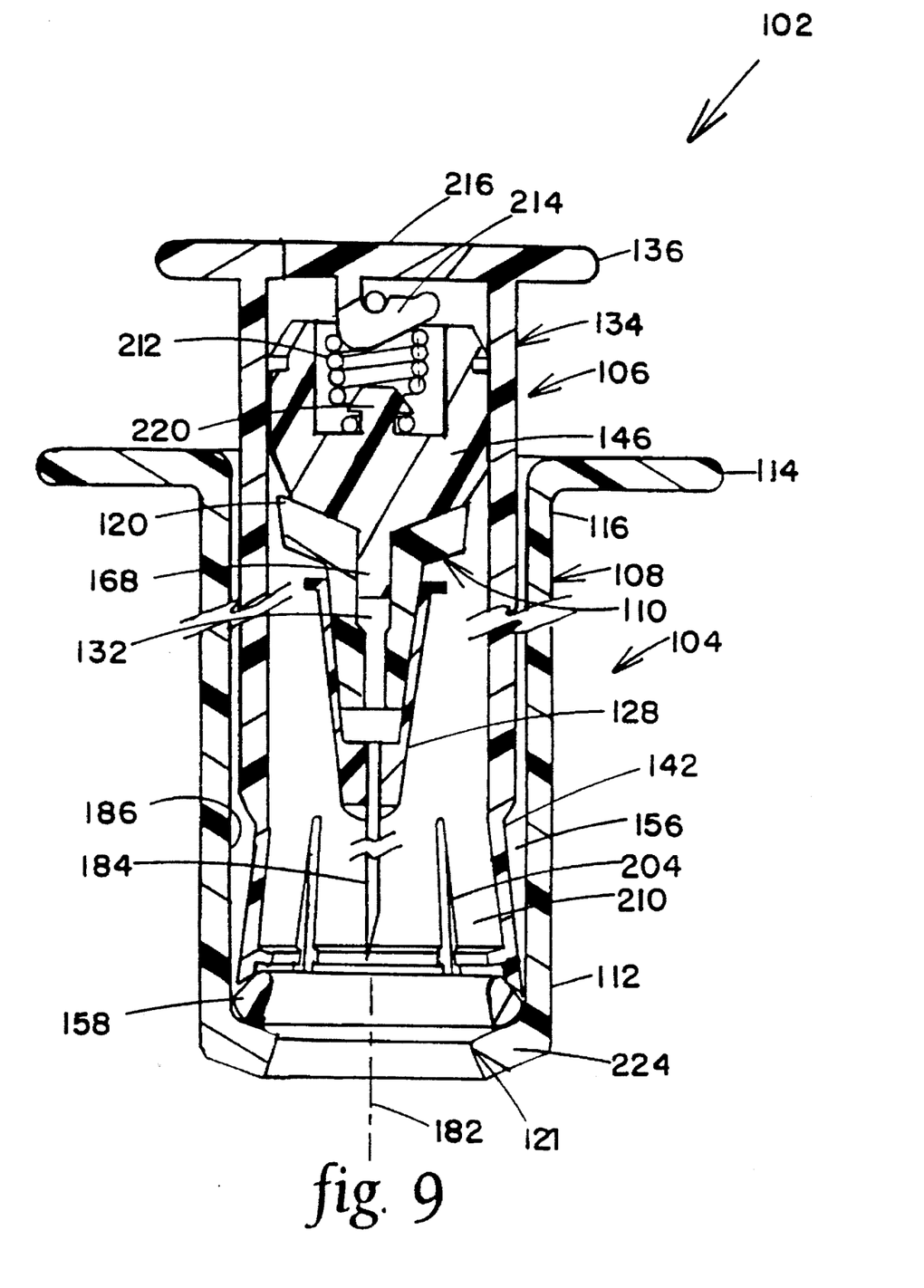
FIG. 9 shows the syringe of FIG. 8 after the plunger has been placed in the second or distal position, as suggested in phantom lines in FIG. 9A, thus allowing the spring within the stem to automatically withdraw the piston body, barrel tip, and needle assembly into the hollow stem and barrel.
Figure 9A:
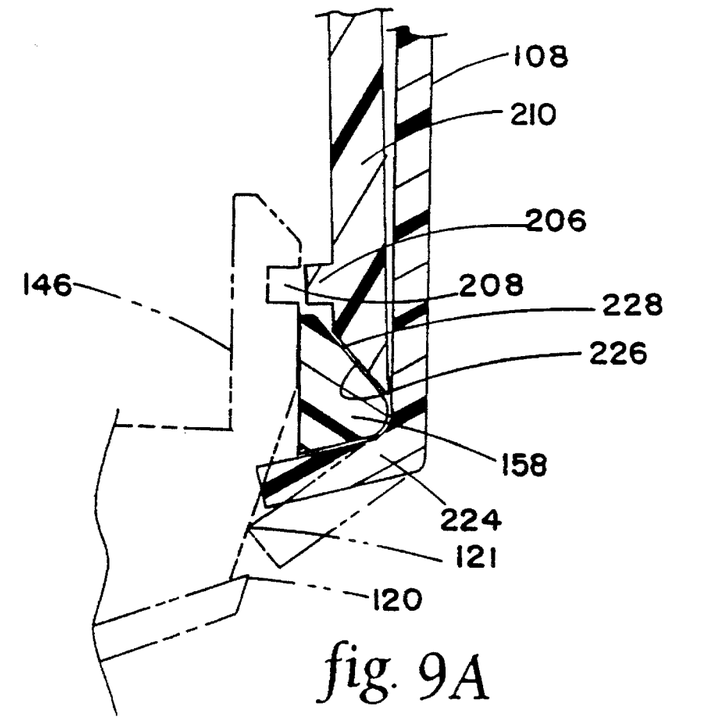
FIG. 9A is an enlarged view of the distal portion of the barrel illustrating the position of the piston body and the barrel tip at the moment the piston body has been released from the distal end of the stem and just prior to the spring pulling the piston body, barrel tip and needle assembly into the hollow stem and barrel.

Syringe 102 is used in essentially the same manner as a conventional syringe. To use syringe 102, which may or may not come with a needle assembly 128 mounted to extension 126 of tip 110, syringe 102 is filled with an appropriate amount of a liquid pharmaceutical by pulling plunger 106 in proximal direction 170 relative to barrel 104. This creates a partial vacuum within interior 156 by virtue of piston seal 158 creating a fluid seal against inner surface 186. The injection is then given in a conventional manner. At the end of the injection stroke, that is with plunger 106 in the second or distal position of FIG. 8, several things happen. As with the embodiment of FIGS. 1–5, piston frangible connection 160 is first severed, in this case by the engagement of piston seal 158 with an inwardly extending lip 224 of side wall 108. Next, barrel frangible connection 124 is severed. This condition is shown in FIGS. 8 and 8A. Continued distal movement of plunger 106 causes the tapered distal edge 226 of stem 134 to engage a complementary proximally facing surface 228 of piston seal 158, causing arms 210 to pivot radially outwardly as shown in FIG. 9A, thus causing projections 206 to be removed from receptacles 208 allowing spring 212 to pull piston body 146, tip 110 and needle assembly 128 therewith into interior 202 of stem 134 and also into interior 156 of barrel 104. This last position is shown in FIG. 9. Syringe 102 is now ready for safe disposal.

Modification and variation can be made to the disclosed embodiments without departing from the subject of the invention as defined in the following claims. For example, inwardly tapering annular surfaces 64, 164 are illustrated as conical surfaces; they could be curved as well. While a conventional friction fit type of needle assembly 128 is shown, other types of needle assemblies could be used. Also, needle 184 could be made as a part of the barrel tip so that the needle assembly could, for example, include only a needle cannula permanently fixed to the barrel tip. Spring 212 is a tension spring; however, by appropriately reconfiguring portions of plunger 106, a compression spring could be used as well. Syringe 2 could be modified to add a conventional locking element at inner surface 86 of barrel 4 adjacent stop 54 to prevent re-use of the syringe after stem 34 has been pulled to a fully proximal position. Spring 212 could be made strong enough to deform the piston seal and pull the entire piston into interior 202 once the plunger is at the second or distal position and the piston has been released from the stem.

What is claimed is:

1. A safety syringe, for use with a hollow needle, comprising:

a barrel including a side wall, having a distal end and an inner surface, and a tip, at the distal end of the side wall, to which the needle is mountable;

a plunger including a stem, having a distal end, and a piston at the distal end of the stem, the piston including a piston body and a piston seal extending from the piston body which sealably engages the inner surface of the barrel, the plunger movable from a first position, with the piston spaced apart from the tip, and a second position, with the piston adjacent the tip;

means for detaching the tip and any needle therewith from the side wall when the plunger has been moved to the second position;

means for connecting the piston to the detached tip when the plunger is at the second position; and means for eliminating sliding contact between the piston seal and the inner surface of the barrel after the plunger has been moved to the second position and while the plunger is moved from the second position;

whereby the piston body and the detached tip and any said needle therewith can be moved into the barrel.

2. The safety syringe of claim 1 wherein the piston seal includes a surface against which a radially outwardly directed fluid force is applied to the piston seal when the plunger is moved from the first position to the second position during use.

3. The safety syringe of claim 1 wherein the piston seal is an integral member with the piston body.

4. The safety syringe of claim 1 wherein the piston seal is connected to the piston body by a frangible connection.

5. The safety syringe of claim 4 wherein the frangible connection has a length and the strength of the frangible connection varies along said length.

6. The safety syringe of claim 4 wherein the sliding contact eliminating means includes means for disconnecting the piston seal from the piston body.

7. The safety syringe of claim 6 wherein the sliding contact eliminating means includes means for disconnecting the piston seal from the piston body before the detaching means has detached the tip from the remainder of the barrel.

8. The safety syringe of claim 6 wherein the barrel includes a recess adjacent the tip sized to receive the disconnected piston seal to retain said piston seal adjacent the tip when the plunger moves back towards the first position.

9. The safety syringe of claim 8 wherein the recess is formed in the side wall.

10. The safety syringe of claim 4 wherein the frangible connection is an annular region.

11. The safety syringe of claim 10 wherein the piston has an inwardly tapering annular surface with a distal portion of a first diameter and a proximal portion of a second diameter.

12. The safety syringe of claim 11 Wherein:

the frangible connection couples an outer circular edge of the tip to an inner circular edge of the remainder of the barrel;

the first diameter is smaller than the inner circular edge and the second diameter is larger than the inner circular edge; and the tapering annular surface is positioned to contact the inner circular edge to dilate the inner circular edge when the plunger is at the second position to aid movement of the tip back through the inner circular edge and into the barrel.

13. The safety syringe of claim 1 wherein the connecting means includes a receptacle within the tip and a plug extending from the piston, the plug sized to be frictionally coupled to the tip when forced into the receptacle.

14. The safety syringe of claim 13 wherein the plug has a generally cylindrical outer surface.

15. The safety syringe of claim 13 wherein the plug and the receptacle are oriented at an angle to one another when the plunger is at the first position so that when the plug is forced into the receptacle upon movement of the plunger to the second position, the detached tip and said any needle therewith will be canted relative to the side wall of the barrel.

16. The safety syringe of claim 1 further comprising means for canting the detached tip and said any needle therewith relative to the side wall of the barrel upon movement of the plunger to the second position.

17. The safety syringe of claim 1 further comprising means for automatically withdrawing the piston body and the detached tip and said any needle therewith into the barrel when the plunger is in the second position.

18. A safety syringe, for use with a needle, comprising:

a barrel including a side wall, having a distal end and an inner surface, and a tip at the distal end of the side wall, to which the needle is mountable;

a plunger including a stem, having a distal end, and a piston at the distal end of the stem, the stem having a hollow stem interior, the piston including a piston body and a piston seal, the piston body being releasably attached to the distal end of the stem, the piston seal being connected to the piston body, the piston seal sealably engaging the inner surface as the plunger moves from a first position, with the piston spaced apart from the tip, to a second position, with the piston adjacent the tip;

means for detaching the tip and any needle therewith from the side wall when the plunger has been moved to the second position;

means for connecting the piston to the detached tip when the plunger is at the second position;

the hollow stem interior being sized to fully house the piston body and the detached tip;

means for disconnecting the piston seal from the piston body upon movement of the plunger to the second position so to eliminate sliding contact between the piston seal and the inner surface; and means for automatically detaching the piston body from the distal end of the stem when the plunger is at the second position and then drawing the piston body and the detached tip and said any needle therewith into said hollow stem interior, the automatically detaching and drawing means including:

a spring coupling the piston body and the stem;

a dilatable distal end of the stem; and means for dilating said distal end of the stem when the plunger is at the second position so that the spring automatically draws the piston body and the tip and said any needle therewith into the hollow stem interior.

19. A safety syringe, for use with a needle, comprising:

a barrel including a side wall, having a distal end and an inner surface, and a tip, connected to the distal end of the side wall by a barrel frangible connection, to which the needle is mountable;

a plunger including a stem, having a distal end, and a piston at the distal end of the stem, the piston including a piston body and a piston seal, connected to the piston body by a piston frangible connection, which sealably engages the inner surface as the plunger moves from a first position, with the piston spaced apart from the tip, to a second position, with the piston contacting the tip;

means for rupturing the barrel frangible connection thereby detaching the tip and any needle therewith from the side wall when the plunger has been moved to the second position;

means for connecting the piston to the detached tip solely through axial movement of the plunger to the second position; and means for rupturing the piston frangible connection thereby disconnecting the piston seal from the piston body upon movement of the plunger to the second position so to eliminate sliding contact between the piston seal and the inner surface while the plunger is moved from the second position towards the first position so to reduce resistance to said movement from the second position to the first position;

whereby the piston body and the detached tip and any said needle therewith can be moved into the barrel.

20. A safety syringe, for use with a needle, comprising:

a barrel including a side wall, having a distal end and an inner surface, and a tip, connected to the distal end of the side wall by a barrel frangible connection, to which the needle is mountable;

a plunger including a stem, having a distal end, and a piston at the distal end of the stem, the stem having a hollow stem interior, the piston including a piston body and a piston seal, the piston body being releasably attached to the distal end of the stem, the piston seal being connected to the piston body by a piston frangible connection, the piston seal sealably engaging the inner surface as the plunger moves from a first position, with the piston spaced apart from the tip, to a second position, with the piston contacting the tip;

means for rupturing the barrel frangible connection thereby detaching the tip and any needle therewith from the side wall when the plunger has been moved to the second position;

means for connecting the piston to the detached tip solely through the axial movement of the plunger to the second position;

the hollow stem interior being sized to fully house the piston body and the detached tip;

means for rupturing the piston frangible connection thereby disconnecting the piston seal from the piston body upon movement of the plunger to the second position so to eliminate sliding contact between the piston seal and the inner surface; and means for automatically detaching the piston body from the distal end of the stem when the plunger is at the second position and then drawing the piston body and the detached tip and said any needle therewith into said hollow stem interior, the automatically detaching and drawing means including:

a spring coupling the piston body and the stem;

a dilatable distal end of the stem; and means for dilating said distal end of the stem when the plunger is at the second position so that the spring automatically draws the piston body and the tip and said any needle therewith into the hollow stem interior.

21. A method for delivery of a liquid pharmaceutical from a syringe and making the syringe safe for disposal, the syringe of the type including a barrel and a plunger, the plunger including a stem and a piston, the piston including a piston body and a piston seal carried by the piston body, the barrel including a tip at a distal end thereof to which a needle is mounted, comprising the following steps:

filling the barrel with a quantity of liquid pharmaceutical;

dispensing the liquid pharmaceutical by forcing the plunger axially into the barrel from a first position to a second position so to drive the liquid pharmaceutical through the needle;

disengaging the tip of the barrel from the remainder of the barrel upon moving the plunger to the second position;

mechanically coupling the tip to the plunger;

moving the disengaged tip and the needle therewith into the barrel; and eliminating sliding contact between piston seal and the barrel during the moving step to aid the movement of the disengaged tip and the needle therewith into the barrel.

22. The method of claim 21 wherein the filling step is accomplished by drawing said quantity of the liquid pharmaceutical through the needle and into the barrel.

23. The method of claim 21 wherein the disengaging step is carried out by moving the plunger against the tip to separate the tip from the remainder of the barrel along a frangible connection connecting the two.

24. The method of claim 23 further comprising the step of dilating an opening in the remainder of the barrel created at the frangible connection when the tip separates from the remainder of the barrel so the tip moves freely through said opening during the moving step.

25. The method of claim 21 wherein the disengaging and mechanically coupling steps are each carried out using only axial motion of the plunger.

26. The method of claim 21 wherein the moving step is carried automatically once the plunger is in the second position.

27. The method of claim 26 wherein the disengaged tip and needle therewith are moved into a hollow interior of the stem during the moving step using a spring carried by the stem.

28. The method of claim 21 wherein the eliminating step includes the step of separating the piston seal from the piston body.

29. The method of claim 28 wherein the separating step occurs as the plunger moves to the second position.

30. The method of claim 28 wherein the separating step is carried out by rupturing a frangible region coupling the piston seal to the piston body.

31. The method of claim 30 wherein the eliminating step includes the step of keeping the separated piston seal at the distal end of the barrel during the moving step.

32. A method for delivery of a liquid pharmaceutical from a syringe and making the syringe safe for disposal, the syringe of the type including a barrel and a plunger, the plunger including a stem and a piston, the piston including a piston body and a piston seal carried by the piston body, the barrel including a tip at a distal end thereof to which a needle is mounted, comprising the following steps:

filling the barrel with a quantity of liquid pharmaceutical;

dispensing the liquid pharmaceutical by forcing the plunger axially into the barrel from a first position to a second position so to drive the liquid pharmaceutical through the needle;

disengaging the tip of the barrel from the remainder of the barrel by forcing the plunger against the tip thereby rupturing a barrel frangible connection between the tip and the remainder of the barrel upon moving the plunger to the second position;

mechanically coupling the tip to the plunger;

automatically moving the disengaged tip and the needle therewith into a hollow interior of the stem and the barrel once the plunger is in the second position using a spring carried by the stem; and separating the piston seal from the piston body by rupturing a piston frangible connection between the piston seal and the piston body thereby eliminating sliding contact between piston seal and the barrel during the automatically moving step so to reduce frictional drag which would otherwise hinder the movement of the disengaged tip and the needle therewith into the barrel.

* * * * *